United States Patent
Klingner

(10) Patent No.: US 6,670,313 B1
(45) Date of Patent: Dec. 30, 2003

(54) METHOD AND COMPOSITION FOR MINIMIZING PERCUTANEOUS ABSORPTION OF INDUSTRIAL CHEMICALS

(75) Inventor: Thomas D. Klingner, Prospect Heights, IL (US)

(73) Assignee: Colormetric Laboratories, Inc., Des Plaines, IL (US)

( * ) Notice: Subject to any disclaimer, the term of this patent is extended or adjusted under 35 U.S.C. 154(b) by 234 days.

(21) Appl. No.: 09/871,187

(22) Filed: May 31, 2001

Related U.S. Application Data

(60) Provisional application No. 60/209,499, filed on Jun. 5, 2000.

(51) Int. Cl.[7] .................................................. C11D 3/44
(52) U.S. Cl. ....................... 510/130; 510/137; 510/138; 510/157; 510/159; 510/407
(58) Field of Search .................................. 510/407, 417, 510/130, 137, 138, 157, 159; 424/401, 59

(56) References Cited

U.S. PATENT DOCUMENTS

| | | | |
|---|---|---|---|
| 3,795,624 A | | 3/1974 | Feinstone |
| 4,239,781 A | | 12/1980 | Edwards |
| 4,496,357 A | | 1/1985 | Osburn |
| 4,533,545 A | | 8/1985 | Sebag |
| 4,968,448 A | * | 11/1990 | Svarz |
| 5,202,357 A | | 4/1993 | Bowser et al. |
| 5,308,526 A | | 5/1994 | Dias et al. |
| 5,462,691 A | | 10/1995 | Shimada et al. |
| 5,558,806 A | * | 9/1996 | Policello et al. |
| 5,763,386 A | | 6/1998 | Mondin et al. |
| 5,792,739 A | | 8/1998 | He et al. |
| 5,798,330 A | | 8/1998 | Misselyn et al. |
| 5,811,107 A | | 9/1998 | Gangadharan et al. |
| 5,837,274 A | | 11/1998 | Shick et al. |
| 5,837,661 A | | 11/1998 | Evans et al. |
| 5,856,284 A | | 1/1999 | Hamada et al. |
| 5,871,764 A | | 2/1999 | Diaz et al. |
| 5,882,666 A | | 3/1999 | Averill et al. |
| 5,891,449 A | | 4/1999 | Daniel et al. |

OTHER PUBLICATIONS

"In Vivo Evaluation of MDI Skin Decontamination Procedures," Wester et al., Polyurethanes Expo '98 (1998).
"Evaluation of Compounds as Barriers to Dermal Penetration of Organophosphates Using Acetylcholinesterase Inhibition," (1990).
Olson et al. Toxicology Letters, 55, pp. 325–334 (1991).

\* cited by examiner

*Primary Examiner*—Gregory Webb
(74) *Attorney, Agent, or Firm*—Seyfarth Shaw LLP

(57) ABSTRACT

A person's skin is protected from percutaneous absorption of lipophilic or semi-polar contaminant chemicals by applying to the skin a plural-constituent solvent system, wherein each constituent has a molecular weight greater than or equal to 350 and includes at least one solvent in which the contaminant chemicals are soluble. The solvent system may include one or more emulsifiers to facilitate water-rinsing of the solvent system and any dissolved contaminant chemicals from the skin. Oil-based and glycol-based solvent systems are disclosed, each having at least two solvents which may have different solubility ranges. The solvent system may be applied to the skin before exposure to contaminant chemicals to serve as a barrier or after exposure to serve as s cleanser. The solvent system includes no water, emollients or detergents and all constituents are skin-safe.

21 Claims, No Drawings

METHOD AND COMPOSITION FOR MINIMIZING PERCUTANEOUS ABSORPTION OF INDUSTRIAL CHEMICALS

RELATED APPLICATION

This application claims the benefit of the filing date of copending U.S. Provisional Application No. 60/209,499, filed Jun. 5, 2000.

BACKGROUND

This invention relates to industrial safety and, in particular, to techniques for minimizing percutaneous absorption of toxic chemicals.

Skin exposure to toxic chemicals has always been a problem. To prevent skin exposure to chemicals, gloves or other protective clothing have been worn. Such gloves, however, are cumbersome to wear and have caused allergic reactions and other problems.

Heretofore, when non-protected skin was contacted with harmful toxic chemicals ("contaminant chemicals"), the skin would typically be flushed with copious amounts of water or with soap and water (as routinely recommended by most material safety data sheets) to try to cleanse the skin of the contaminant chemical and prevent percutaneous absorption thereof. Though this may have been useful for skin exposed to hydrophilic chemicals, it was not efficient for removing from the skin chemicals which are not soluble in water (lipophilic) or only slightly soluble in water (semi-polar). In fact, rinsing with water may actually increase the percutaneous absorption of such chemicals.

Though it is known that common lipophilic chemicals are more soluble in lipophilic solvents than water, the application of common lipophilic solvents to the skin to remove contaminant chemicals therefrom has not been successful because, as discussed below, these solvents penetrate or diffuse across the skin and allow the contaminant chemical to be carried across the skin.

The ability of a chemical to be absorbed through the skin depends on two primary chemical characteristics, its solubility relative to water and its molecular size.

The outermost layer of the skin, the stratum corneum, consists mainly of highly keratinized dead skin cells held together by interstitial layers of lipids. The primary function of the stratum corneum is to retain moisture in the body and provide a physical barrier to infectious bacteria and viruses. Thus, the skin is a highly effective barrier to the absorption or loss of water and water soluble (hydrophilic) chemicals.

The ability, or lack thereof, of a chemical to partition into the stratum corneum is the initial limiting step in determining the dermal penetration rate (Kp). Since like materials dissolve like materials, the stratum corneum is most permeable to fat soluble (lipophilic) chemicals because of its layers of lipids.

The second characteristic determining the dermal penetration rate (Kp) is the molecular size of the chemical contaminant. Molecular size generally increases with the molecular weight (MW) of the chemical. Chemicals with high molecular weights, such as those greater than 350, are significantly limited in their ability to permeate the stratum corneum due to their physical size, while lower molecular weight chemicals more easily permeate the stratum corneum.

Thus, low molecular weight lipophilic chemicals that are insoluble or poorly soluble in water are readily absorbed through the skin.

Solvents for removing contaminant chemicals from the skin should be chosen based on their ability to dissolve those chemicals. The solubility of a chemical in a solvent is determined by it octanol/water partition coefficient (log K o/w). Solvents with a log K o/w value similar to that of a contaminant chemical will readily dissolve the chemical.

An appropriate solvent is important because the partition coefficient of a contaminant chemical, Ksc/Kv (Ksc, solubility in the stratum corneum, vs Kv, solubility in the solvent), defines the equilibrium ratio of the concentration of the compound in the stratum corneum to that in the adjacent application solvent (trying to dissolve the chemical). Therefore, a contaminant chemical with a higher affinity (solubility) for a solvent that is applied on the skin will partition more slowly into the stratum corneum. Therefore, one would believe that solvents which readily dissolve a contaminant chemical would, when applied to skin contacted with the contaminant, dissolve the contaminant chemical and limit percutaneous absorption thereof.

This concept, however, is valid only if the solvent itself does not affect the absorption properties of the skin (damage the stratum corneum) and if the solvent itself does not diffuse across the stratum corneum. If the solvent does diffuse across the stratum corneum, it acts as a carrier or active transport of the contaminant chemical being absorbed. Therefore, though a contaminant chemical may have a much higher solubility in a low molecular weight lipophilic solvent than in the stratum corneum, the low molecular weight lipophilic solvent could not be used to prevent percutaneous absorption of the chemical because the low molecular weight lipophilic solvent would be absorbed into the stratum corneum and act as a carrier for the chemical.

Disrupting the stratum corneum significantly increases the percutaneous absorption of chemical exposure, thereby contributing to the development of irritant or allergic dermatitis. Thus, skin cleansers incorporating harsh detergents which can damage the skin tend to increase the potential for skin absorption of chemical exposure. The addition of cosmetic emollients or "moisturizers" to such cleansers can further promote chemical absorption. Commonly used additives, such as aloe vera and isoproplymyristate are rapidly absorbed into the stratum corneum. Moreover, these additives have been proven to be effective vehicles to enhance the absorption efficacy of lipohilic drugs. D-limonene, widely employed in citrus-based skin cleansers, has been shown to be among the most effective penetration enhancers for dermal drug delivery.

Thus, to date, there have been no completely satisfactory methods for minimizing the percutaneous absorption of lipophilic or semi-polar chemicals which have been in contact with the skin.

OSHA also recognized that there have been no such satisfactory methods. On Aug. 10, 1992, OSHA promulgated a final rule, 29 CFR, parts 1910 and 1926, Occupational exposure to 4,4' methylenedianiline (MDA). OSHA recognized in assessing exposure risk that "in certain situations approximately 95% of exposure results from dermal absorption." OSHA further stated "MDA cannot be completely removed by cleansing. The data suggest that the use of solvents to remove MDA from the skin actually increases the absorption of MDA. It also appears that soap and water provide the best medium for removing the substance from the skin but only removes 60% of the material deposited on the skin."

The final standard requires that "workers subjected only to dermal exposure to MDA must be instructed to immediately wash exposed areas with soap and water or any medium which does not increase the absorption properties of MDA. This particular requirement was given much consideration by OSHA."

The comments to the rule make it clear that OSHA did not want to require that only soap and water be used to remove MDA impregnated resin or accumulations on the skin because something better might be developed in the future. OSHA believed that if a particular solvent could be demonstrated not to increase the absorption properties of MDA it should be used to remove MDA from the skin. OSHA, did not, however, suggest any such solvent.

SUMMARY

This application discloses an improved technique for minimizing percutaneous absorption of contaminant chemicals exposed to the skin, which avoids the disadvantages of prior technologies.

An important aspect is the provision of a method of the type set forth, which uses a solvent system which is comprised essentially entirely of high-molecular-weight compounds which have limited ability to diffuse through the skin.

Yet another aspect is the provision of a method of the type set forth, which utilizes a solvent system in which the contaminant chemical has a high solubility.

Still another aspect is the provision of a method of the type set forth, which utilizes a solvent system which can be rinsed from the skin with water.

A still further aspect is the provision of a method of the type set forth, wherein the solvent system includes an emulsifier.

Another aspect is the provision of a method of the type set forth, in which the solvent system eliminates the use of water, emollients, and detergents.

A further aspect is the provision of a method of the type set forth which minimizes the damage to the skin.

In connection with the foregoing aspects, another aspect is the provision of a solvent system of the type set forth.

Certain ones of these and other aspects may be attained by providing a solvent system for dissolving contaminant chemicals on a person's skin comprising: at least one skin-safe solvent in which the contaminant chemicals are soluble, and one or more additional constituents, wherein each constituent in the system has a molecular weight of at least 350.

The method and solvent system consist of certain novel features and a combination of parts hereinafter fully described, it being understood that various changes in the details may be made without departing from the spirit, or sacrificing any of the advantages of the subject matter sought to be protected.

DETAILED DESCRIPTION

This application discloses a method and composition to minimize percutaneous absorption of non-polar (lipophilic) and semi-polar chemicals by applying a non-aqueous solvent system to the skin as a barrier prior to exposure to the chemicals or as a cleansing solution after skin exposure to the chemicals. The solvent system has an average molecular weight of at least 350. In particular, the solvent system is formed essentially of all high-molecular weight ("HMW"), skin-safe constituents, each having a molecular weight of at least 350, and preferably greater than 400. These HMW chemicals, as discussed above, have little ability to permeate the stratum corneum. The method is especially useful in minimizing or preventing the percutaneous absorption of industrial chemicals, such as aromatic amines, isocyanates, pesticides, oils, grease, paints and the like. Preferably, at least about 75 weight % of the solvent system is formed of HMW constituents, and most preferably as close to 100 weight % as possible. Each solvent system is specifically formulated to be able to optimally dissolve predetermined contaminant chemicals in contact with the skin to efficiently remove non-polar and semi-polar chemicals from the skin while minimizing deleterious effects to the skin's natural barrier function. In this regard, solvent systems are formulated to dissolve chemicals within a range of octanol/water partition coefficients (log K o/w). Thus, individual solvent systems can be formulated to best dissolve lipophilic chemicals with a high log K o/w or can be formulated to best dissolve chemicals having a lower log K o/w. The solvent systems are also formulated to be able to be rinsed from the skin with water and may, accordingly, include a HMW emulsifier. Examples of solvent systems for minimizing percutaneous absorption of lipophilic and semi-polar chemicals are discussed below.

Oil-based Lipophilic (non-polar) Solvent Formulation

To remove highly lipophilic (log K o/w>3.0) chemicals from the skin, a liquid or semi-solid solvent system ("oil-based solvent system") is applied to the skin. The oil-based solvent system is comprised of skin-safe constituents each having a molecular weight of at least 350, and preferably greater than 400, and which is formulated to be able to dissolve these lipophilic chemicals. The oil-based solvent system preferably has a maximum solubility for chemicals with a log K o/w in the range of from about 4.5 to about 6.5.

The solvent system is preferably comprised of a first solvent, such as one or more triglycerides (preferably one or more natural plant oils) and/or a methyl ester of a high-molecular weight fatty acid (C22 or greater, such as high euricic acid rapeseed oil); a second solvent, such as polypropylene glycol (average molecular weight of at least 350) or a similar solvent, such as a polyalkoxylated polyether or block polyol, and one or more emulsifiers (preferably non-ionic food or cosmetic grade) to enable the oil-based solvent system to be rinsed from the skin with water. Non-active additives, such as preservatives, stabilizers, viscosity modifiers, fragrance and colorants can be included for appearance and shelf life.

Preferred plant oils include soybean, corn, olive, canola, cotton seed, sunflower or other common plant oils, in either their natural or hydrogenated form. The triglyceride(s) comprises from about 10 to about 90 weight %, preferably from about 30 to about 70 wt. %, of the solvent system.

The second solvent is preferably less lipophilic than the plant oil to broaden the solubility range of the solvent system. Preferred second solvents include polypropylene glycols (having an average molecular weight of from about 350 to about 2000, preferably from about 425 to about 700) and polyester or polyether based solvents. The second solvent preferably comprises from about 10 to about 70 weight % of the oil-based solvent system, and more preferably from about 20 to about 45 wt. %.

Preferred emulsifiers include any of a range of common non-ionic surfactants having a molecular weight of at least 350, including food grade emulsifiers such as polyoxyethylene sorbitan esters (polysorbates), sorbitan esters, polyoxyethylene ethers, polyhydric alcohol esters, polyethylene glycol esters or glycerol esters. The emulsifiers enhance the water rinseability of the oil-based solvent system. Preferably, the emulsifier comprises from about 2.5 to about 20 weight % of the solvent system.

Examples of the oil-based solvent system are set forth below:

EXAMPLE 1

| Component | Weight % |
|---|---|
| Soybean oil | 55 |
| Polypropylene Glycol (MW 700) | 30 |
| PEG 400 Dioleate | 10 |
| PEG 400 Monooleate | 5 |

EXAMPLE 2

| Component | Weight % |
|---|---|
| Corn oil | 55 |
| Polyalkoxylated polyether (Macol 625) | 35 |
| Polysorbate 85 | 7.5 |
| PEG 400 Dioleate | 7.5 |

EXAMPLE 3

| Component | Weight % |
|---|---|
| high euracic acid rapeseed oil methyl ester | 50 |
| polypropylene glycol (avg. molecular weight 425) | 30 |
| polysorbate 80 | 10 |
| polyethylene glycol 400 dioleate | 10 |

These oil-based solvent systems are effective in removing harmful chemical contaminants having a log K o/w exceeding 3.0, such as toluene diisocyanate, benzo-a-pyrene, methylene bis phenyl diisocyanate, pentachlorophenol, chlorpyrifos, polychlorobenzenes, DDT, diesel oil, parathion, toluene, benzene, aldrin, lindane and malathion.

Glycol Based (semi-polar) Solvent System Formulation

A liquid or semi-solid solvent system for the removal of semi-polar (log K o/w −0.5 to 4.0) chemical species ("semi-polar solvent system") from the skin has an average molecular weight of at least 350 and, preferably, is comprised of skin-safe constituents each having a molecular weight of at least 350, and preferably greater than 400, and which system is formulated to be able to dissolve these semi-polar chemicals. The semi-polar solvent system preferably has a maximum solubility for chemicals with a log K o/w from about 1.5 to about 2.5. The semi-polar solvent system preferably includes polyethylene glycol (PEG), polypropylene glycol (PPG) and one or more surfactant emulsifiers. The semi-polar solvent system can also include non-active additives to affect appearance or shelf life of the semi-polar solvent system.

The preferred average molecular weight of the PEG is from about 350 to about 1500. Below 350, the smaller molecular size results in increased percutaneous absorption. Above molecular weight 1500, the PEG is a viscous solid limiting its solvent action. The PEG comprises from about 20 to about 80 weight %, preferably from about 40 to about 70 weight % of the semi-polar solvent system.

The preferred average molecular weight of the PPG is from about 425 to about 2000. Above a molecular weight of 500, PPG become increasingly water insoluble (lipophilic). This increasingly non-polar character limits its solvency function for semi-polar chemicals. PPG comprises from about 10 to about 60 weight %, preferably from about 20 to about 40 weight % of the solvent system.

Other chemical solvents, such as polyalkoxylated polyethers and block polyols may be used in place of or in addition to PEG and PPG, to change the solvent system's log K o/w or solubility characteristics needed to dissolve the contaminant chemical(s) on the skin.

The semi-polar solvent system also includes one or more surfactant emulsifiers, preferably non-ionic or mild high-molecular-weight ionic species to improve water rinseability and solvent function. The preferred surfactant emulsifiers have a molecular weight of at least 350, preferably greater than 400, and may be non-ionic surfactants, such as polysorbates, polyoxyethylene ethers, polyethylene glycol esters and block polymers, or mild ionic surfactants. The surfactant emulsifier comprises from about 5 to about 30 weight %, preferably about 10 weight % of the semi-polar solvent system.

Examples of several semi-polar solvent system formulations are below:

EXAMPLE 4

| Component | Weight % |
|---|---|
| PEG 400 | 50 |
| PPG 425 | 40 |
| Polysorbate 80 | 5.0 |
| PEG 400 Monooleate | 5.0 |

EXAMPLE 5

| Component | Weight % |
|---|---|
| PEG 400 | 30 |
| PEG 600 | 15 |
| PPG 425 | 25 |
| PPG 700 | 15 |
| Polysorbate 60 | 7.5 |
| PEG 400 Dioleate | 7.5 |

EXAMPLE 6

| Component | Weight % |
|---|---|
| PEG 400 | 60 |
| Polyalkoxylated polyether(Macol 660) | 30 |
| PEG Monolaurate | 10 |

The semi-polar based solvent system is effective in removing harmful chemical contaminants with a log K o/w from about −0.5 to about 4, such as aldrin, lindane, malathion, aniline, dinitrotoluene, nitroaniline, trinitrobenzene, dichloroethane, captan, methyleneischloroaniline, methylenedianiline, phenol, acrylonitrile and acetone.

Use of the Solvent Systems

When a person's skin is contacted with a contaminant chemical, an appropriate solvent system, described above, which will dissolve the chemical is applied to the affected area of the skin. The solvent system is then simply rinsed off with water. The solvent system can be reapplied and rinsed off again as necessary.

Alternatively, the solvent system can be used as a barrier and applied to the person's skin prior to the person using or coming in contact with dangerous chemicals. The appropriate solvent system is chosen based upon the log K o/w of the chemicals to which a user will be exposed. When a dangerous chemical contacts the skin, the solvent system is washed off with water, and reapplied, as necessary.

The matter set forth in the foregoing description and accompanying drawings is offered by way of illustration only and not as a limitation. While particular embodiments have been shown and described, it will be obvious to those skilled in the art that changes and modifications may be made without departing from the broader aspects of applicant's contribution. The actual scope of the protection sought is intended to be defined in the following claims when viewed in their proper perspective based on the prior art.

I claim:

1. An emollient-free non-aqueous solvent system for dissolving toxic chemicals on a person's skin comprising:
    a skin-safe first solvent having an average molecular weight of at least 350 so as to minimize its skin permeability and a maximum solubility for first contaminant chemicals which have an octanol/water partition coefficient (log K o/w) in a first range, and
    a skin-safe second solvent having an average molecular weight of at least 350 so as to minimize its skin permeability and a maximum solubility for second contaminant chemicals which have a log K o/w in a second range different from the first range,
    at least one of the first and second ranges being less than 3.5.

2. The solvent system of claim 1, wherein the solvent system is oil-based.

3. The solvent system of claim 2, wherein the first solvent is selected from the group consisting of triglycerides and methyl esters of high-molecular-weight fatty acids.

4. The solvent system of claim 3, wherein the second solvent is selected from the group consisting of polypropylene glycol, polyalkoxylated polyether, and block polyol.

5. The solvent system of claim 1, wherein the solvent system is glycol based.

6. The solvent system of claim 5, wherein the solvents are selected from the group consisting of polyethylene glycol, polypropylene glycol, polyalkoxylated polyesters and bock polyols.

7. The solvent system of claim 1, wherein the first solvent comprises from about 10 weight % to about 90 weight % of the solvent system and the second solvent comprises from about 10 weight % to about 70 weight % of the solvent system.

8. The solvent system of claim 7, wherein the first solvent comprises from about 30 weight % to about 70 weight % of the solvent system and the second solvent comprises from about 20 weight % to about 45 weight % of the solvent system.

9. The solvent system of claim 7, wherein the first solvent comprises from about 40 weight % to about 70 weight % of the solvent system and the second solvent comprises from about 20 weight % to about 40 weight % of the solvent system.

10. The solvent system of claim 1, wherein each of the solvents has an average molecular weight of at least 400.

11. The solvent system of claim 1, wherein the first range is less than 3.5 and the second range is greater than 3.5.

12. The solvent system of claim 1, wherein both of the first and second ranges are less than 3.5.

13. An emollient-free non-aqueous solvent system for dissolving lipophilic contaminant toxic chemicals on a person's skin comprising:
    a skin-safe first solvent having an average molecular weight of at least 350 so as to minimize its skin permeability and a maximum solubility for lipophilic contaminant chemicals which have an octanol/water partition coefficient (log K o/w) in a first range,
    a skin-safe second solvent having an average molecular weight of at least 350 so as to minimize its skin permeability and a maximum solubility for lipophilic contaminant chemicals which have a log K o/w in a second range different from the first range, and
    a skin-safe emulsifier having a molecular weight of at least 350,
    at least one of the first and second ranges being less than 3.5.

14. The solvent system of claim 13, wherein the emulsifier is selected from the group consisting of polysorbates, sorbitan esters, polyoxyethylene esters, polyhydric alcohol esters, polyethylene glycol esters, and glycerol esters.

15. The solvent system of claim 13, wherein the emulsifier is selected from a group consisting of non-ionic surfactants and mild ionic surfactants.

16. The solvent system of claim 13, wherein the emulsifier is a first emulsifier, and further comprising a second emulsifier different from the first emulsifier and having a molecular weight of at least 350.

17. The solvent system of claim 16, wherein the emulsifiers comprise from about 2.5 weight % to about 20 weight % of the solvent system.

18. The solvent system of claim 16, wherein the emulsifiers comprise from about 5 weight % to about 30 weight % of the solvent system.

19. The solvent system of claim 18, wherein the emulsifiers comprise about 10 weight % of the solvent system.

20. The solvent system of claim 13, wherein the solvent system is oil-based.

21. The solvent system of claim 13, wherein the solvent system is glycol based.

* * * * *